United States Patent [19]

Petitpierre et al.

[11] 4,011,237
[45] Mar. 8, 1977

[54] HETEROCYCLIC SUBSTITUTED CHROMENOPYRAZOLES

[75] Inventors: Jean Claude Petitpierre, Kaiseraugst, Switzerland; Robert Garner, Bury, England

[73] Assignee: Ciba-Geigy Corporation, Ardsley, N.Y.

[22] Filed: Oct. 24, 1975

[21] Appl. No.: 625,731

[30] Foreign Application Priority Data

Nov. 13, 1974 Switzerland .............. 15130/74

[52] U.S. Cl. .............................. 260/310 R
[51] Int. Cl.² ............................ C07D 491/02
[58] Field of Search ........................ 260/310 R

[56] References Cited

FOREIGN PATENTS OR APPLICATIONS

| 2,018,169 | 5/1970 | France |
| 1,946,848 | 4/1970 | Germany |
| 2,441,595 | 3/1975 | Germany |
| 2,036,817 | 1/1972 | Germany |

*Primary Examiner*—Donald B. Moyer
*Attorney, Agent, or Firm*—Joseph G. Kolodny; Edward McC. Roberts; Prabodh I. Almaula

[57] ABSTRACT

Heterocyclic substituted chromenopyrazoles having the general formula

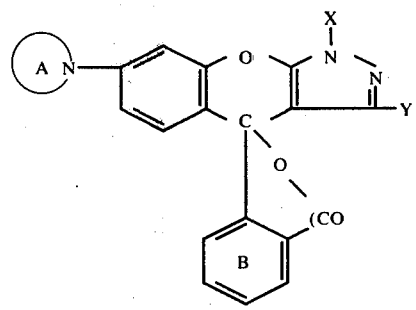

wherein
the nitrogen-containing ring A represents a heterocyclic radical which may contain a further heteroatom in the ring,
X and Y, independently of the other, represent alkyl of 1 to 12 carbon atoms, alkoxy of 1 to 12 carbon atoms, phenyl or phenyl which is substituted by alkyl of 1 to 4 carbon atoms, nitro, halogen, amino or by an amino group which is mono or disubstituted by alkyl of 1 to 12 carbon atoms, acyl of 2 to 12 carbon atoms or by benzyl, and
wherein the benzene ring B is unsubstituted or is substituted by a nitro group or by 1 to 4 halogen atoms. These chromenopyrazoles are particularly useful as color formers which give strong orange, orange red or brownish orange colors when they are brought into contact with an electron-accepting co-reactant.

7 Claims, No Drawings

HETEROCYCLIC SUBSTITUTED CHROMENOPYRAZOLES

The present invention provides chromenopyrazoles which contain heterocyclic substituents, a process for their manufacture and a method of using these compounds in pressure-sensitive or thermoreactive (heat-sensitive) recording or copying material.

The chromenopyrazoles according to the invention have the general formula

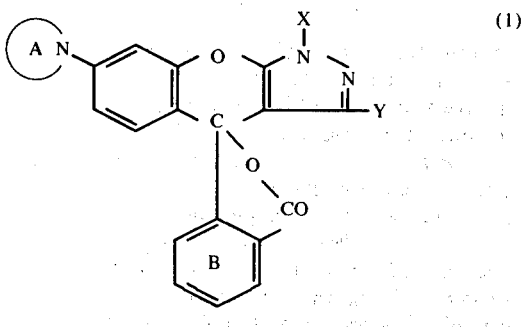

wherein the nitrogen-containing ring A represents a heterocyclic radical which may contain a further heteroatom in the ring, in particular an oxygen, sulphur or nitrogen atom, X and Y, which can be the same or different, represent alkyl of 1 to 12 carbon atoms, alkoxy of 1 to 12 carbon atoms, phenyl or phenyl which is substituted by alkyl of 1 to 4 carbon atoms, preferably methyl, or by nitro, halogen, or by an amino group which can be mono- or disubstituted by alkyl of 1 to 12 carbon atoms, acyl of 2 to 12 carbon atoms or by benzyl, and wherein the benzene ring B can be substituted by a nitro group or 1 to 4 halogen atoms.

In the chromenopyrazoles of formula (1) the ring A represents a heterocyclic ring which is attached to the chromenopyrazole system through the nitrogen atom. The ring A can contain 3 to 15, preferably 5 or 6, ring members, and as ring member a second heteroatom can also be present. The nitrogen-containing ring A is, for example, a pyrrolidinyl, piperidino, α,β- or γ-pipecolino, perhydroazepinyl, heptamethylenimino, octamethylenimino, 1,2,3,4-tetrahydroquinolinyl, indolinyl or hexahydrocarbazolyl group, or, if the heteroring B contains a further heteroatom, can be a morpholino, thiomorpholino, piperazino, N-alkylpiperazino group of 1 to 4 carbon atoms in the alkyl moiety, or a pyrazolinyl or 3-methylpyrazolinyl group.

As alkyl or alkoxy groups, X and Y preferably represent methyl, methoxy or ethoxy. The alkyl moieties in the N-substituted aminophenyl radicals X and Y are, for example, methyl, ethyl, n-butyl, n-hexyl, n-octyl or n-dodecyl. Especially preferred acyl groups herein are the alkanoyl groups of 2 to 4 carbon atoms, such as acetyl or propionyl. Halogen atoms are, for example, fluorine, bromine or preferably chlorine.

The benzene ring B is preferably not further substituted or it contains a nitro group. In the latter case, the nitro group of the phthalic anhydride radical is in 4-, 5-, 6- or 7-position and the nitro-chromenopyrazoles can be in the form of mixtures of these isomers. Preferred isomeric mixtures of these nitrochromenopyrazoles are mixtures of two isomers in which the nitro groups of the phthalic anhydride radical are either in the 4- and 7-positions or in 5- and 6-positions.

Preeminent chromenopyrazole compounds of the class defined by formula (1) are those of the general formula

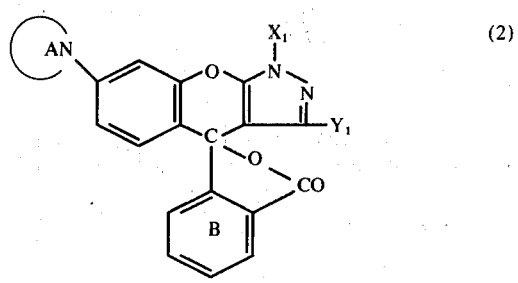

wherein the rings A and B are as defined in formula (1), $X_1$ represents alkyl of 1 to 4 carbon atoms, phenyl or phenyl which is substituted by alkyl of 1 to 4 carbon atoms, nitro, halogen or by an amino group which can be mono- or disubstituted by alkyl of 1 to 4 carbon atoms, alkanoyl of 2 to 4 carbon atoms or by benzyl, and $Y_1$ represents alkyl of 1 to 3 carbon atoms preferably methyl or phenyl. The ring A in formula (1) or (2) preferably represents a 5- or 6-membered heterocyclic ring and in particular is a piperidino, morpholino or most preferably a pyrrolidinyl radical.

The alkyl, nitro or amino substituent in the substituted phenyl radical $X_1$ is preferably in para-position to the nitrogen atom of the pyrazole ring.

The most preferred compounds are chromenopyrazoles of the general formula

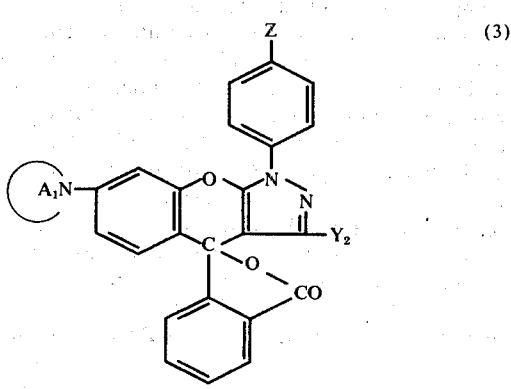

wherein the nitrogen-containing ring $A_1$ is a morpholino or preferably a pyrrolidino or piperidino ring, $Y_2$ represents methyl or phenyl and Z represents hydrogen, methyl or nitro.

Preferred compounds of formula (3) are those in which the ring $A_1$ represents a pyrrolidinyl radical.

The chromenopyrazoles according to the invention of formula (1) are new compounds and can be manufactured by methods which are known per se. One process for the manufacture of the chromenopyrazoles of formula (1) comprises reacting a benzophenone compound of the general formula

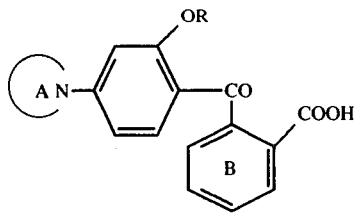  (4)

wherein R represents alkyl of 1 to 4 carbon atoms, e.g. methyl, or preferably hydrogen, and the rings A and B are as defined in formula (1), with a pyrazolone of the general formula

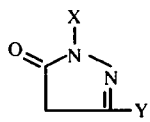  (5)

The reaction is advantageously carried out in the presence of an acid condensing agent. Examples of suitable condensing agents are acetic anhydride, phosphoric acid, phosphoroxy chloride, anhydrous zinc chloride or preferably sulphuric acid with for example a concentration above 60% by weight. As a rule substantially equimolar amounts of the reactants are condensed, preferably at a temperature in the range of 50° to 130° C. Upon termination of the condensation, the reaction mixture is poured into a substantial amount of ice water and the precipitated product is filtered off and treated with aqueous alkali, to yield the compounds of formula (1) as colourless crystals.

Chromenopyrazoles of formula (1), wherein X or Y or X and Y are N-substituted aminophenyl radicals, can also be manufactured for example by reacting a compound of formula (1), wherein at least one of the radicals X and Y represents an aminophenyl radical, with a reactive ester of an alkanol or benzyl alcohol and an inorganic or organic acid. Examples of such reactive esters are: methyl, ethyl, n-propyl, n-butyl or benzyl esters of hydrochloric, hydrobromic and hydriodic acid, dimethyl and ethyl sulphate. Alternatively, the compounds of formula (1) can also be reacted with a reactive functional derivative of a carboxylic acid, especially fatty acid halides and anhydrides, for example acetyl chloride, acetyl bromide or acetic anhydride.

The starting materials of formula (4) are as a rule manufactured by reacting a phthalic anhydride of formula

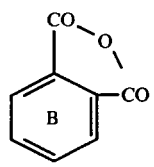  (6)

with a compound of formula

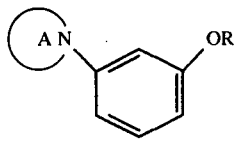  (7)

wherein R and the rings A and B are as defined hereinbefore. This reaction is advantageously carried out in an organic solvent, for example acetone, benzene, toluene, xylene or in a chlorobenzene, preferably at the boiling point of the solvent or below it. If the phthalic anhydride compound of formula (6) contains a nitro group, then it is preferably the 3- or 4-nitrophthalic anhydride or a mixture of these two isomers.

The compounds of formula (7) can be manufactured by condensing a heterocyclic base

, wherein the ring A has the indicated meaning, with resorcinol or a monoalkyl ether thereof at a temperature between 50° and 250° C and, if appropriate, under pressure. This reaction can be carried out in the presence or absence of a condensing agent. Examples of suitable condensing agents are: zinc chloride, aluminium chloride or sulphanilic acid. Alternatively, the compounds of formula (7) can also be obtained by reacting m-hydroxyaniline or m-alkoxyaniline with a α,ω-dihaloalkane the halogen atoms of which are, for example, chlorine or preferably bromine.

The chromenopyrazoles of formulae (1) to (3) are colourless compounds which are suitable for use as colour formers when brought into contact with an acid active substance, i.e. an electron acceptor substance. Typical examples of such coreactants are attapulgite clay, silton clay, silica, bentonite, halloysite, aluminium oxide, aluminium sulphate, aluminium phosphate, kaolin or any acid clay, or an acid polymeric material, for example a phenolic polymer, an alkylphenolacetylene resin, a maleic acid/rosin resin or a partially or completely hydrolysed polymer of maleic acid and styrene, ethylene, vinyl methyl ether or carboxypolymethylene. Preferred coreactants are attapulgite clay, silton clay or phenolformaldehyde resin. These electron acceptors are preferably applied in the form of a layer to the face of the receiver sheet.

It is possible to produce different colours with these colour formers, mostly strong orange, orange red or brownish orange colourations. When used with other known colour formers, they are in particular useful for achieving grey or black tints.

The chromenopyrazoles of the present invention constitute a novel class of colour formers whose solubilities are such that a wide choice of solvents is available for encapsulating and other purposes. This can be advantageous for example when encapsulating the colour formers.

The colour formers of the present invention are suitable above all for use in pressure-sensitive copying and recording material. Such a material comprises for example at least a pair of sheets that contain at least one colour former of formulae (1) to (3) dissolved in an organic solvent and an electron acceptor as developer. The colour former effects a coloured marking at those points at which it comes into contact with the electron acceptor substance.

These colour formers which are present in the pressure-sensitive recording material are separated from the electron acceptor substance in order to prevent them from becoming active too soon. This can be accomplished as a rule by incorporating the colour formers in foam-like, sponge-like or honeycomb-like structures. Preferably, however, the colour formers are enclosed in microcapsules which can be burst by pressure.

When the capsules are burst by pressure, for example with a pencil, and the colour former solution is thus transferred to an adjacent sheet, a coloured zone is produced. This colour results from the dye which is thereby formed and which absorbs in the visible range of the electromagnetic spectrum.

A number of processes for the manufacture of microcapsules have long been known. Such known processes are described, for example, in U.S. Pat. Nos. 2 183 053, 2 797 201, 2 800 457, 2 800 458, 2 964 331, 3 016 308, 3 171 878, 3 265 630, 3 405 071, 3 410 250, 3 418 656, 3 424 827 and 3 427 250. Further processes are described in British patent 989 264 and above all in British patents 1 156 725, 1 301 052 and 1 355 124. All these and other processes are suitable for encapsulating the colour formers of the present invention.

The colour formers are encapsulated preferably in the form of solutions in organic solvents. Examples of suitable solvents are preferably non-volatile solvents, for example polyhalogenated diphenyl, such as trichlorophenyl and a mixture thereof with liquid paraffin, tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of naphthalene or diphenyl, terphenyls, partially hydrogenated terphenyl, or other chlorinated or hydrogenated condensed aromatic hydrocarbons. The capsule walls can be formed evenly around the droplets of the colour former solution by coacervation, in which case the encapsulating material can consist of gelatin and gum arabic, as described e.g. in U.S. Pat. No. 2 800 457.

The capsules can be formed preferably also from an aminoplast or from modified aminoplasts by polycondensation, as described in the British patents cited above.

A preferred arrangement consists in applying the encapsulated colour formers as a layer to the back of a transfer sheet and the electron acceptor substance as a layer to the face of a receiving sheet. It is also possible to add other known colour formers, for example crystal violet lactone, 3,3-bis-(1'-n-octyl-2'-methylindol-3'-yl)-phthalide or benzoylleucomethylene blue.

The microcapsules containing the colour formers of formula (1) can be used for the manufacture of pressure-sensitive copying materials of the most widely different known kinds. The various systems differ substantially from one another in the arrangement of the capsules, the colour reactants and the carrier material.

The microcapsules can be contained in a bottom layer of the top sheet and the developer, i.e. the electron acceptor, in the coating layer of the bottom sheet. The components can, however, also be used in the paper pulp.

Such pressure-sensitive copying materials are described, for example, in U.S. Pat. Nos. 2 730 457, 2 932 582, 3 418 250, 3 418 656, 3 427 180 and 3 516 846. Further systems are described in British patent Nos. 1 042 596, 1 042 597, 1 042 598, 1 042 599, 1 053 935 and 1 517 650. Microcapsules which contain the colour formers of formula (1) are suitable for each of these systems and for other systems.

The capsules are preferably secured to the carrier by means of a suitable adhesive. Since paper is the preferred carrier material, these adhesives are principally paper coating agents, for example gum arabic, polyvinyl alcohol, hydroxymethyl cellulose, casein, methyl cellulose or dextrin.

The term "paper" used herein comprises not only normal paper made from cellulose fibres, but also paper in which the cellulose fibres are replaced (partially or completely) by synthetic polymer fibres.

The new chromenopyrazoles can also be used in a thermoreactive recording material. This contains normally at least a carrier, a colour former, an electron acceptor substance and optionally a binder. Thermoreactive recording systems comprise heat-sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks.

The thermoreactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor substance at those points at which heat is applied and the desired colour develops at once.

The developers are the same electron-accepting substances as are used in pressure-sensitive papers. For practical purposes the developer should be solid at room temperature and melt or soften above 50° C. Examples of such products are the clays or phenolic resins already mentioned, or phenolic compounds, for example 4-tert.butylphenol, 4-phenylphenol, 4-hydroxydiphenyl oxide, α-naphthol, β-naphthol, 4-hydroxybenzoic acid methyl ester, 4-hydroxyacetophenol, 2,2'-dihydroxydiphenyl, 4,4-isopropylidene-diphenol, 4,4'-isopropylidene-bis-(2-methylphenol), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and aliphatic dicarboxylic acids, e.g. tartaric acid, oxalic acid, maleic acid, citric acid, citraconic acid or succinic acid.

Fusible, film-forming binders are preferably used for the manufacture of the thermoreactive recording material. These binders should be able to disperse and fix the colour former and the developer at room temperature.

By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylic amide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyl resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further additives. The coatings can contain, for example, talc, $TiO_2$, ZnO or $CaCO_3$ for improving the degree of whiteness, facilitating the printing of papers, and for preventing the heated pen from sticking. In order to effect the colour formation only within a limited temperature range, it is possible to add substances such as urea, thiourea, acetanilide, phthalic anhydride or other appropriate fusible products which induce the simultaneous melting of the colour former and developer.

Typical thermoreactive recording materials in which the colour formers according to the invention can be used are described, for example, in German Offenlegungsschriften Nos. 2 110 864 and 2 228 581, in French patent No. 1 524 826 and in Swiss patents No. 164 976, 407 185, 444 196 and 444 197.

The following Examples illustrate the invention, the percentages being by weight unless otherwise stated.

EXAMPLE 1

A mixture of 9.33 g of 2-hydroxy-4-N-pyrrolidinyl-2-carboxybenzophenone, 6.82 g of 1,3-diphenyl-5-pyrazolone and 40 ml of 98% sulphuric acid is stirred for 4 hours at 60° C. The resultant solution is poured onto 350 ml of ice water. The precipitate is filtered off, washed neutral and recrystallised from methanol. Yield: 10.9 g of the chromenopyrazole of formula

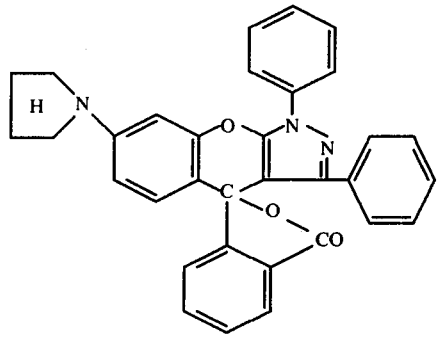

(11)

This substance melts at 248°–250° C and has a λ maximum at 508 nm in 95% acetic acid. When brought into contact with silton clay this colour former has λ maxima at 495 and 517 nm.

EXAMPLE 2

The procedure of Example 1 is repeated with 0.94 g of 1-p-methyl-phenyl-3-methyl-5-pyrazolone being substituted for the 1,3-diphenyl-5-pyrazolone used therein. The chromenopyrazole of formula

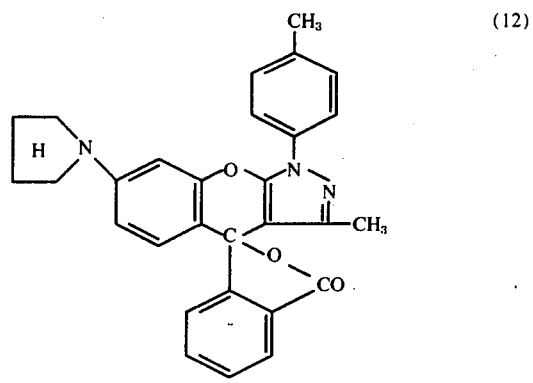

(12)

is obtained with a melting point of 279°–281° C. A solution of this colour former in 95% acetic acid has a λ maximum at 505 nm. When this substance comes in contact with silton clay it has a λ maximum value of 505 nm.

EXAMPLE 3

The procedure of Example 1 is repeated with 0.87 g of 1-phenyl-3-methyl-5-pyrazolone being substituted for the 1,3-diphenyl-5-pyrazolone used therein. The chromenopyrazole of formula

(13)

is obtained with a melting point of 306°–308° C. A solution of this compound in 95% acetic acid has a λ maximum at 502 nm. When this colour former comes in contact with silton clay it has a λ maximum value of 505 nm.

EXAMPLE 4

The procedure of Example 1 is repeated with 1.08 g of 1-p-nitrophenyl-3-methyl-5-pyrazolone being substituted for the 1,3-diphenyl-5-pyrazolone used therein. The chromenopyrazolone compound of formula

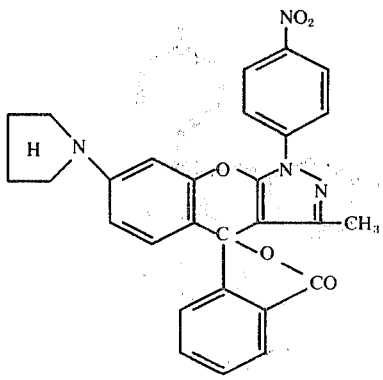

(14)

is obtained with a melting point above 310° C. The λ maximum in 95% acetic acid is 510nm. On silton clay this dye develops an orange red shade with adsorption maxima at 497 and 523 nm.

EXAMPLE 5

The procedure of Example 1 is repeated with 6.3 g of 1-(m-chlorophenyl)-3-methyl-5-pyrazolone being substituted for the 1,3-diphenyl-5-pyrazolone used therein. The chromenopyrazole of formula

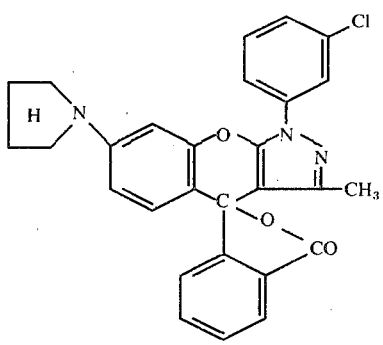

(15)

is obtained with a melting point of 215° C.

A solution of this compound in 95% acetic acid has a λ maximum at 563 nm. In contact with silton clay this colour former has a λ maximum value of 510 nm.

EXAMPLE 6

Manufacture of a pressure-sensitive copying paper

A solution of 3 g of the chromenopyrazole compound of formula (11) in 97 g of partially hydrogenated terphenyl is emulsified in a solution of 12 g of pigskin gelatin in 88 g of water of 50° C. A solution of 12 g of gum arabic in 88 g of 50° C is then added and then 200 ml of water of 50° C. The resultant emulsion is poured into 600 g of ice water and cooled until the temperature is 20° C, in the course of which the coacervation is effected. A sheet of paper is coated with the resultant suspension of microcapsules and dried. A second sheet of paper is coated with silton clay. The first sheet and the sheet of paper coated with silton clay are laid on top of each other with the coated sides face to face.

Pressure is exerted by writing by hand or with a typewriter on the first sheet and an orange red copy of excellent light fastness is developed on the sheet coated with silton clay.

Corresponding effects can be obtained by using each of the other colour formers of Examples 2 to 5.

EXAMPLE 7

Manufacture of a thermoreactive paper 6 g of an aqueous dispersion which contains 1.57% of the chromenopyrazole of formula (12) and 6.7% of polyvinyl alcohol are mixed with 134 g of an aqueous dispersion which contains 14% of 4,4-isopropylidenediphenol and 6% of polyvinyl alcohol. This mixture is applied to a paper and dried. Contacting the paper with a heated ball-point pen produces a vivid orange colour of excellent lightfastness. Similar results are obtained on using any of the other colour formers indicated in Examples 1, 3 to 5.

We claim:

1. A chromenopyrazole of the formula

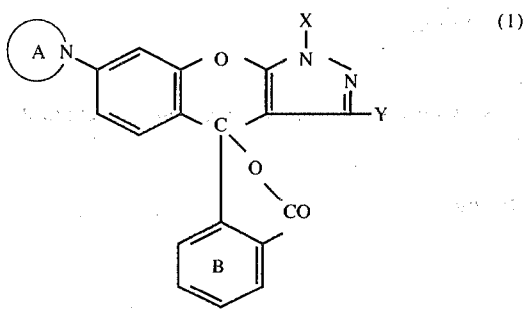

(1)

wherein
the ring A represents pyrrolidinyl,
X and Y, independently of the other, represent alkyl of 1 to 12 carbon atoms, alkoxy of 1 to 12 carbon atoms, phenyl or phenyl which is substituted by alkyl of 1 to 4 carbon atoms, nitro, halogen, amino or by an amino group which is mono- or disubstituted by alkyl of 1 to 12 carbon atoms acyl of 2 to 12 carbon atoms or by benzyl, and
wherein the benzene ring B is unsubstituted or is substituted by a nitro group or by 1 to 4 halogen atoms.

2. A chromenopyrazole according to claim 1 of the formula

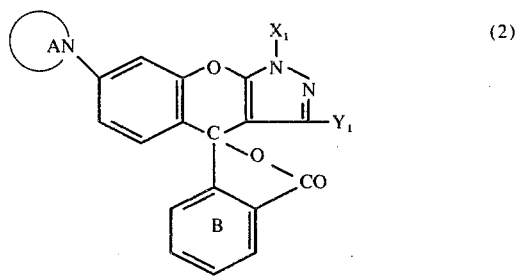

(2)

wherein $X_1$ represents alkyl of 1 to 4 carbon atoms, phenyl or phenyl which is substituted by alkyl of 1 to 4 carbon atoms, nitro, halogen, amino or by an amino group which is mono- or disubstituted by alkyl of 1 to 4 carbon atoms, alkanoyl of 2 to 4 carbon atoms or by benzyl, and $Y_1$ represents alkyl of 1 to 3 carbon atoms or phenyl.

3. A chromenopyrazole according to claim 2 of the formula (2), wherein the alkyl, nitro or amino substituent in the substituted phenyl radical $X_1$ is in para-position to the nitrogen atom of the pyrazole ring.

4. A chromenopyrazole according to claim 2 of the formula (2) wherein A is the pyrrolidinyl radical, $X_1$ is meta-chlorophenyl, $Y_1$ is methyl and the ring B is unsubstituted.

5. A chromenopyrazole according to claim 3 of the formula

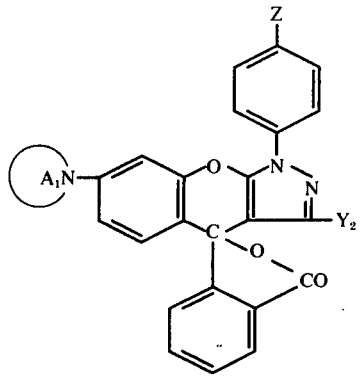

(3)

wherein the ring $A_1$ represents a pyrrolidinyl radical,
$Y_2$ represents methyl or phenyl and
Z represents hydrogen, methyl or nitro.

6. A chromenopyrazole according to claim 5 of the formula (3) wherein $A_1$ represents the pyrrolidinyl radical, Z is hydrogen and $Y_2$ is methyl.

7. A chromenopyrazole according to claim 5 of the formula (3) wherein $A_1$ represents the pyrrolidinyl radical and Z and $Y_2$ both are methyl.

* * * * *